United States Patent [19]
Kushner et al.

[11] Patent Number: 6,117,638
[45] Date of Patent: Sep. 12, 2000

[54] METHODS TO SCREEN FOR TRANSCRIPTION FACTOR-COACTIVATOR INTERACTIONS

[75] Inventors: Peter J. Kushner; Paul Webb; Rosalie M. Uht, all of San Francisco, Calif.

[73] Assignee: The Regents of the University of California, Oakland, Calif.

[21] Appl. No.: 09/054,238

[22] Filed: Apr. 2, 1998

Related U.S. Application Data

[60] Provisional application No. 60/043,059, Apr. 4, 1997.

[51] Int. Cl.[7] .................................. C12Q 1/68; C12Q 1/02
[52] U.S. Cl. .................................................. 435/6; 435/29
[58] Field of Search ............................................ 435/6, 29

[56] References Cited

U.S. PATENT DOCUMENTS 5,789,170   8/1998   Chang et al. .............................. 435/6

OTHER PUBLICATIONS

D. Swope et al. "CREB–binding protein activates transcription through multiple domains" *Journal of Biological Chemistry* (Nov. 8, 1996) 271 (45): 28138–28145.

K.B. Horwitz et al. "Nuclear Receptor Coactivators and Corepressors" *Molecular Endocrinology* (Oct. 1996) 10 (10): 1167–1177.

Hong et al, PNAS (USA), vol. 93, pp. 4948–4952, May 1996.

Peterson et al, Trends in Biotech, vol. 11, pp. 11–18, Jan. 1993.

*Primary Examiner*—Terry McKelvey
*Attorney, Agent, or Firm*—Skjerven, Morrill, MacPherson, Franklin & Friel, LLP; Tom Hunter, Esq.

[57] ABSTRACT

This invention provides methods for modulating gene expression at the transcriptional level. In particular, the methods involve tethering a transcriptional coactivator to a DNA binding domain that is specific for a target nucleic acid sequence and contacting the coactivator with a transcription factor. The transcription factor triggers or represses transcription mediated by the coactivator. Methods for identifying compounds that are able to modulate gene expression are also provided.

14 Claims, 10 Drawing Sheets

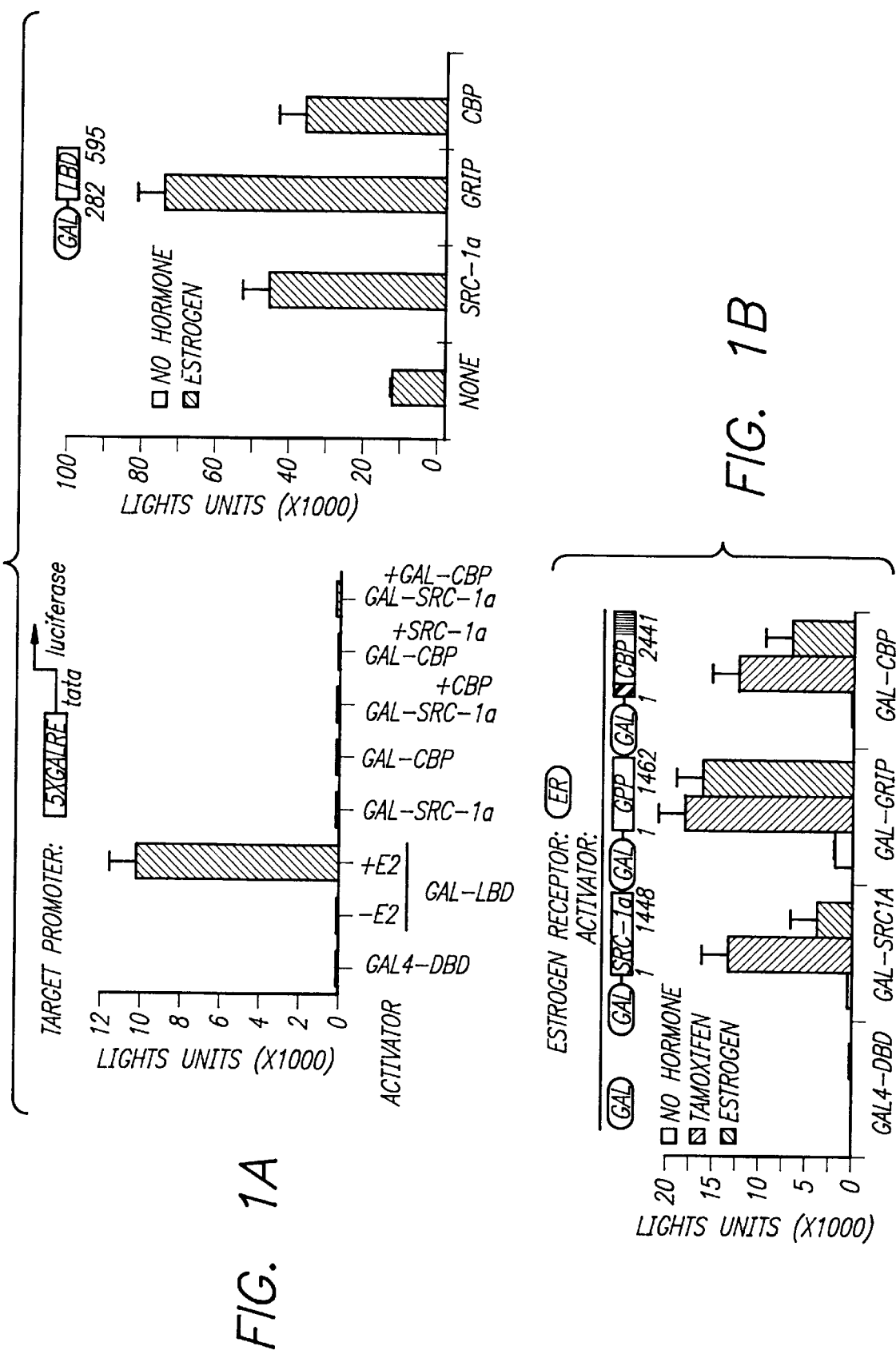

FIG. 4A
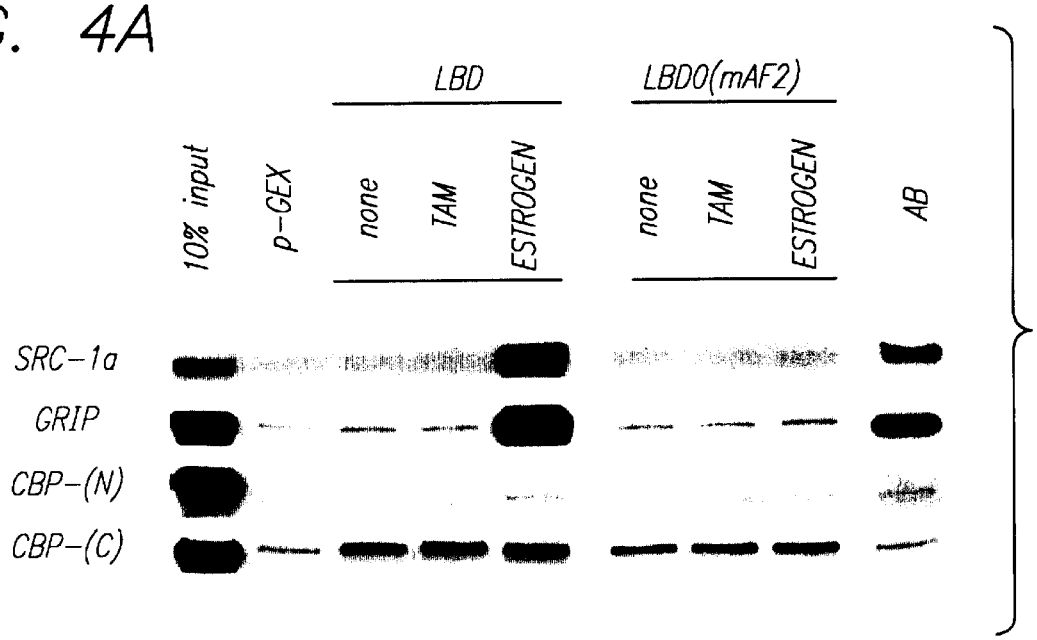
FIG. 4B
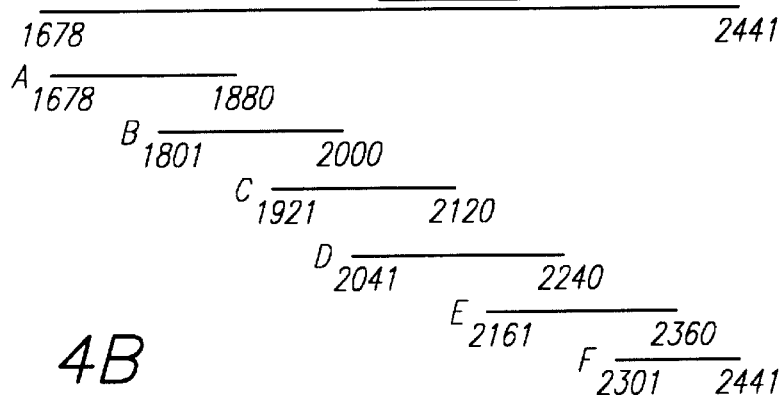
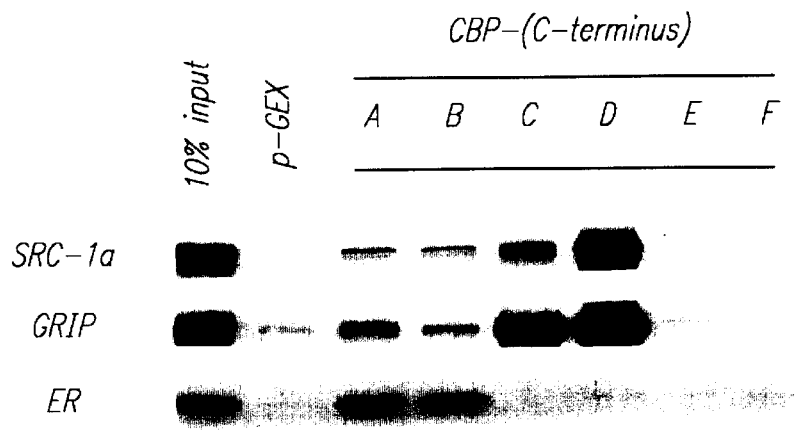

FIG. 6A
Tethered Activator
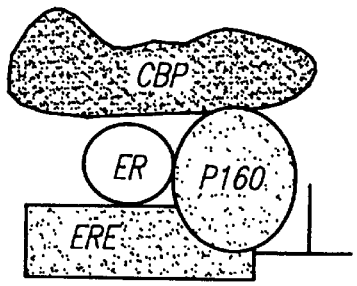
i) recruitment
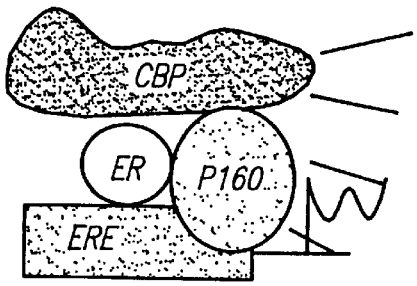
ii) triggering
Tethered Coactivator
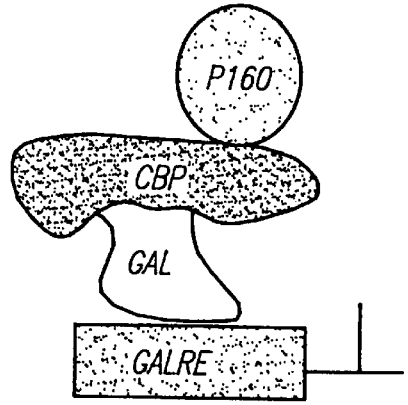
i) prerecruitment
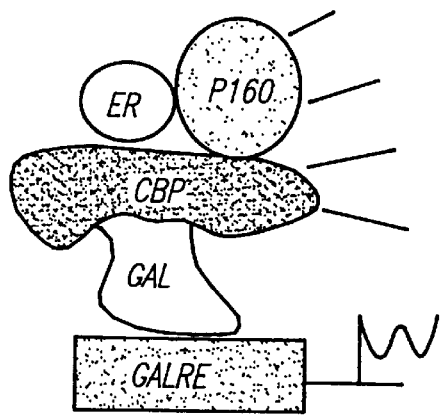
ii) triggering
FIG. 6B

METHODS TO SCREEN FOR TRANSCRIPTION FACTOR-COACTIVATOR INTERACTIONS

CROSS-REFERENCE TO RELATED APPLICATIONS

This application claims the benefit of U.S. Provisional Application Ser. No. 60/043,059, filed Apr. 4, 1997.

STATEMENT REGARDING FEDERALLY SPONSORED RESEARCH

This invention was made with Government support under Grant No. DK51083, awarded by the National Institutes of Health, and Grant No. AIBS 562, awarded by the US Army. The Government has certain rights in this invention.

BACKGROUND OF THE INVENTION

1. Field of the Invention

This invention pertains to the field of modulating gene expression at the transcriptional level. The methods involve tethering a transcriptional coactivator to a DNA binding domain that is specific for a response element, and contacting the coactivator with a transcription factor.

2. Background

Expression of many genes is mediated by signals that increase or decrease transcription of the gene. For example, the presence or absence of a hormone or other compound in or near a cell can switch on or off expression of a particular gene, or family of genes, within the cell. The regulation of gene expression in response to an intracellular or intercellular stimulus is often desirable, such as when such modulation is required for development of the organism or for the ability of the organism to adapt to changes in its environment. However, in some instances gene expression is turned on or off inappropriately. For example, some evidence suggests that estrogen-mediated gene expression is involved in some types of breast and ovarian cancers.

The mechanism by which estrogen and other modulators of transcription exert their effect on gene expression is complex and incompletely understood. In the case of estrogen and other steroid hormones, for example, the hormone binds to a nuclear receptor that is specific for the hormone. The binding of the hormone to the receptor is believed to cause a conformational change that allows the receptor to bind to certain target sites, often referred to as "response elements," that are located upstream of genes that are regulated by the hormone. Additional proteins are involved in regulating transcription mediated by nuclear hormone receptors. The estrogen receptor (ER), for example, binds two classes of coactivator. The first class, referred to as P160s, includes SRC-1a and GRIP-1/TIF-2. These proteins interact with the ligand binding domain (LBD) of nuclear receptors in a manner that is dependent on hormone and the intactness of the LBD trans-activation function, AF2. Onate et al., *Science* 270: 1354–7 (1995); Voegel et al., *EMBO J.* 15: 3667–3675 (1996); Hong et al., *Proc. Nat'l. Acad. Sci. USA* 93: 4948–52 (1996); Halachmi et al., *Science* 264: 1455–1458 (1994); Cavailles et al., *Proc. Nat*l. Acad. Sci. USA 91: 10009–10013 (1994). The second class consists of CBP and the closely related protein P300, which are required for transcriptional activation by CREB, Jun/Fos and a growing list of transcription factors. Kamei et al., *Cell* 85: 403–14 (1996); Chakravarti et al., *Nature* 383: 99–103 (1996); Smith et al., *Proc. Nat'l. Acad. Sci. USA* 93: 8884–8888 (1996); Hanstein et al., *Proc. Nat'l. Acad. Sci. USA* 93: 11540–11545 (1996); Janknecht and Hunter, *Nature* 383: 22–23 (1996). The two types of coactivator are essential for ER-mediated transcriptional activation. Overexpression of members of the p160 family enhance nuclear receptor action, whereas dominant negative SRC-1a and GRIP-1 block nuclear receptor action. Onate et al., supra.; Hong et al., supra. Similarly, overexpression of CBP, or p300, potentiates ER action, whereas micro-injected antibodies against CBP block nuclear receptor action. Kamei et al., supra.; Chakravarti et al., supra. Since the p160s are tightly bound to CBP and p300 in vivo (Kamei et al., supra.; Hanstein et al., supra.), and SRC-1a and CBP bind to both TBP and TFIIB in vitro (Swope et al., *J. Biol. Chem.* 271: 28138–28145 (1996); Kwok et al., *Nature* 370: 223–226 (1994), a model has been hypothesized in which the ER works by recruiting the p160-CBP complex to the promoter, and that this complex forms a bridge to the basal transcription machinery (BTM).

These earlier hypotheses do not, however, explain all observations regarding regulation of gene expression by hormones. For example, tamoxifen and related antiestrogens, which are used to treat hormone-dependent breast cancer, bind to the ER and block its activation by estrogen. However, tamoxifen has the undesirable side effect of activating, rather than repressing, estrogen-regulated genes in certain types of cells such as uterine cells. Webb et al., *Mol. Endocrinol.* 9: 443–456. Promoter regions of genes activated by these antiestrogens were found to have an AP-1 response element, rather than an estrogen response element, but the mechanism by which antiestrogens could exert the paradoxical effect of repressing ER-mediated transcription but activating AP-1-mediated transcription remained unknown. Other estrogen "mimetics" such as certain pesticides and other chemicals may provide an inappropriate signal for certain genes to be expressed or repressed in an undesirable manner, resulting in "feminization" of males. These estrogen mimetics can act like estrogens even though the mimetics appear to be chemically unrelated to estrogen. Other chemicals may inappropriately stimulate or repress the effects of other classes of signaling molecules, such as neurotransmitters and growth factors.

Although methods for modulating gene expression would be highly valuable in treating many conditions, the development of such methods has been hampered by a lack of understanding of the mechanisms by which moieties such as nuclear hormone receptors exert their effects on gene expression. Therefore, a need exists for methods for modulating gene expression, and for identifying compounds that are capable of stimulating or repressing signal-mediated changes in gene expression. The present invention fulfills these and other needs.

SUMMARY OF THE INVENTION

The invention provides methods for stimulating expression of a gene that is regulated by a transcription factor. The methods involve contacting with a tethered coactivator a nucleic acid that includes the gene of interest operably linked to a response element. The tethered coactivator is composed of a polypeptide that comprises an activation function derived from a transcriptional coactivator, and a DNA binding moiety that is capable of specifically binding to the response element. The tethered coactivator is contacted with an activated transcription factor polypeptide that includes an activation function derived from a transcription factor. The contacting of the tethered coactivator with the activated transcription factor polypeptide stimulates expression of the gene. The transcription factor can be, for example, a nuclear hormone receptor such as the estrogen receptor or the estrogen receptor beta, or an AP1 transcription factor.

In another embodiment, the invention provides methods for repressing expression of a gene by contacting a nucleic acid that includes the gene of interest operably linked to a response element with a tethered coactivator. The tethered coactivator includes an activation function derived from a transcriptional coactivator and a DNA binding moiety that is capable of specifically binding to the response element. The tethered coactivator is preactivated and contacted with an activated transcription factor polypeptide that comprises a repressor function derived from a transcription factor. The contacting of the tethered coactivator with the activated transcription factor polypeptide represses expression of the gene.

Another embodiment of the invention provides methods of identifying a test compound that is capable of modulating transcription of a gene of interest. The methods involve providing a nucleic acid that comprises a reporter gene operably linked to a response element and contacting the nucleic acid with a tethered coactivator. The tethered coactivator includes a polypeptide that comprises an activation function derived from a transcriptional coactivator and a DNA binding moiety that is capable of specifically binding to the response element. The tethered coactivator is contacted with a transcription factor polypeptide that comprises an activation function derived from a transcription factor that is involved in modulating expression of the gene of interest in its natural milieu. Prior to contacting the tethered coactivator, the transcription factor polypeptide is contacted with the test compound. Expression of the reporter gene is detected to determine whether the test compound has an effect on transcription.

In another embodiment, the invention provides methods for screening a test compound for the ability to stimulate or repress an indirect estrogen response. The methods involve providing a cell that contains an estrogen receptor and a reporter gene that is regulated by an AP1 site. A tethered coactivator is placed in the cell so that it comes into contact with polypeptides that are associated with the AP1 site. The cell is also contacted with the test compound, and expression of the reporter gene is detected.

BRIEF DESCRIPTION OF THE FIGURES

FIGS. 1A–1B present data which demonstrate that the ER potentiates the activity of its own coactivators. FIG. 1A: Coactivators have no effect on transcription when tethered to DNA. A GAL4 responsive reporter gene was transfected into HeLa cells along with expression vectors for the GAL4-DBD, GAL4-DBD coactivator fusions, or a GAL4 ER-LBD for comparison. Expression vectors for free SRC-1a and CBP were included where indicated. The right panel shows the influence of free coactivators on ER-LBD driven gene expression. FIG. 1B: ER potentiates the activity of tethered coactivators. The transcriptional activity of the GAL4-DBD or GAL4-coactivator fusion proteins was measured in cells that were transfected with ER and treated with either tamoxifen or estrogen. Schematic diagrams of the GAL4-coactivator fusion proteins are shown at the top of the diagram. The striped and shaded boxes in CBP represent the approximate positions of latent activation functions.

FIGS. 2A–2C present data which demonstrate that ER activation of CBP involves p160s. FIG. 2A: ER activation of GAL-CBP is further potentiated by transfected p160s. Transcriptional activity of GAL4-CBP was monitored in cells that were transfected with ER and expression vectors for various native coactivators, and treated with hormones as in FIG. 1B. FIG. 2B: ER activates CBP through the candidate p160 binding site in the CBP carboxy-terminal domain. The effect of ER was measured on the transcriptional activation capacity of GAL4-CBP fusion proteins. The left panel shows ER effects on GAL4-CBP fusions (amino acids 1–460, 227–460 or 1678–2441). The data are expressed as fold induction over activities that were obtained in the absence of ER and hormone. FIG. 2C right panel shows a finer mapping in which ER induction of GAL4-CBP1678-2441 was compared to ER induction of GAL4-CBP fusions bearing shorter regions of the CBP carboxy-terminus. The data are expressed as corrected light units.

FIG. 3A: Expression vectors for full length ER (with or without the valine substitution at position 400), the isolated LBD (amino acids 282–595), an LBD bearing alanine substitutions at positions 543 and 544 (originally methionine and leucine) and a region spanning the AB domain and DBD (amino acids 1–281), were assessed for their ability to potentiate GAL-SRC-1a and GAL-CBP. The star symbol depicts ER expression vectors that contain the wild type glycine residue at position 400. FIG. 3B: The activity of ER activation functions targeted to the GAL4 promoter. Activity of the GAL4 responsive reporter gene in the presence of expression vectors for the GAL4-DBD, an ER in which the GAL4-DBD replaces the ER-DBD (E-GAL-E), and GAL4 fusions to the LBD and AB regions of ER containing AF2 or AF1.

FIGS. 4A–4B present data which demonstrate the interaction of ER activation functions with p160s and CBP. FIG. 4A: Binding of coactivators to ER. The GST fusion proteins were p-GEX (parent vector; commercially available from Pharmacia Biotech), GST-LBD or GST-LBD, with a mutation in AF2, both in the presence of ethanol vehicle, tamoxifen or estrogen respectively, and GST-AB (amino acids 1–184). The input radiolabeled proteins were full length SRC-1a and GRIP-1, the amino-terminal two thirds of CBP and the carboxy-terminal third of CBP. The AF2 mutation converted amino acids 547 and 548 from methionine and leucine, respectively, to alanine. FIG. 4B: SRC-1a/GRIP-1 and ER bind separate sites on the CBP C-terminus. In vitro translated p160s and full length ER were tested for their ability to bind to the fragments of CBP, expressed as GST-fusion proteins, that are depicted at the top. The region that was found to give the strongest response to ER in transfection assays (see FIG. 2B, right panel) is indicated.

FIG. 5A: The effect of transfected empty RSV-driven expression vector, c-Jun, c-Fos, Jun/Fos or Jun ser63,73ala were assessed on the transcriptional activity of GAL-CBP. FIG. 5B: Ligands that initiate second messenger pathways that stimulate the Jun activation function also enhance jun activation of CBP. The experiment was performed as in FIG. 5A. Where indicated, transfected cells were treated with TNFα (10 ng/ml), EGF (10 ng/ml) or PMA (100 nM) or appropriate vehicles.

FIGS. 6A–6B present a model for ER interaction with the coactivator complex. FIG. 6A: ER binds to DNA and the ER transactivation functions synergise to recruit, then trigger transcriptional activity of the coactivator complex (CBP+ P160). FIG. 6B: When the coactivator (CBP) is pre-recruited to DNA the role of ER in recruitment is bypassed and the effect of ER trans-activation functions in triggering the transcriptional activity of coactivators is revealed.

DETAILED DESCRIPTION

Definitions

Figure 2A:
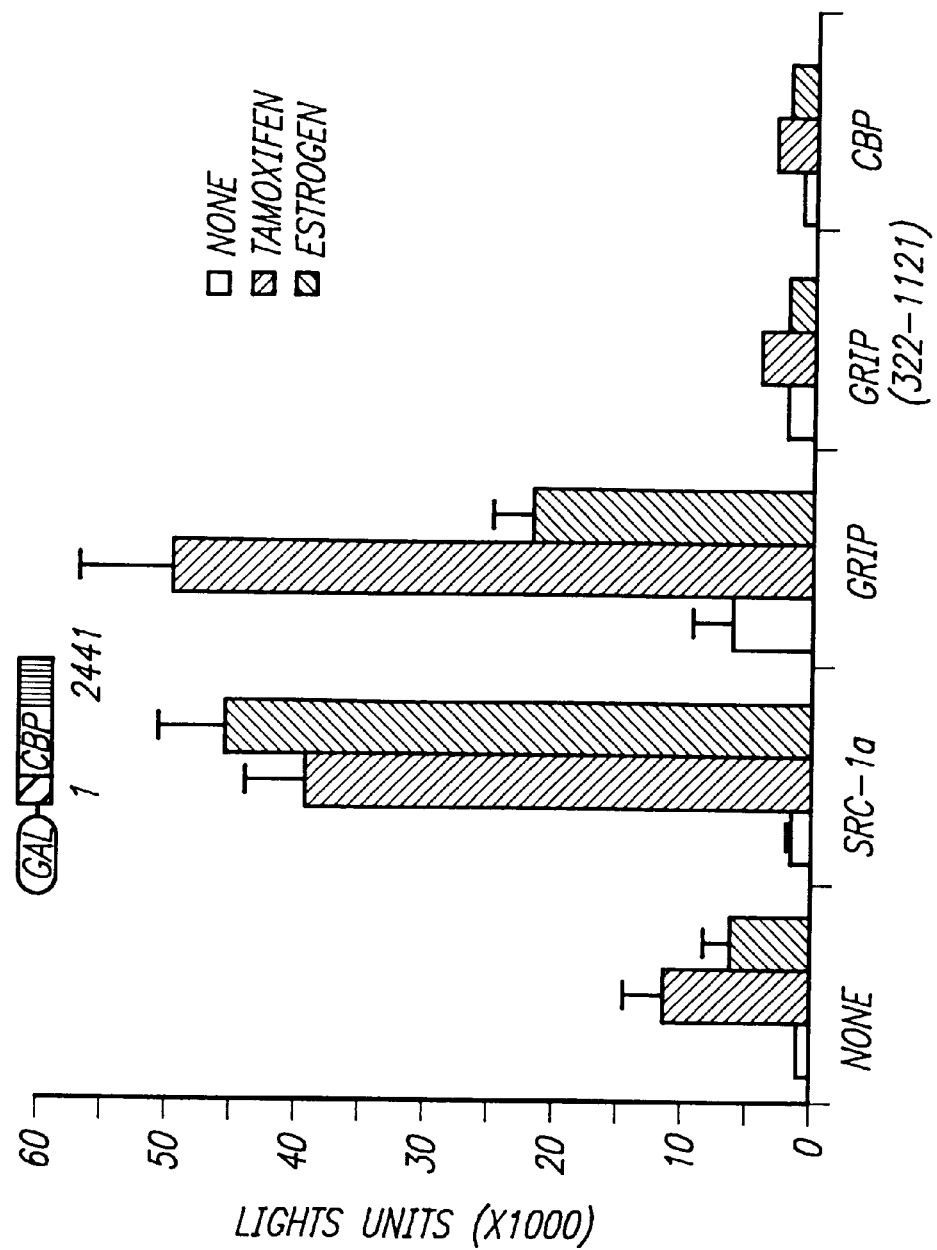

As used herein, a "transcription factor" includes a polypeptide that is involved in stimulating or repressing gene expression. Transcription factors in general are reviewed in Barnes and Adcock, *Clin. Exp. Allergy* 25 Suppl. 2: 46–9 (1995) and Roeder, *Methods Enzymol.* 273: 165–71 (1996). A transcription factor is capable of binding to DNA in the regulatory region of a gene that is expressed under the control, at least in part, of the transcription factor.

An "activation function derived from a transcription factor" refers to that portion of a transcription factor that is capable of stimulating or repressing transcription when the portion comes into contact with a coactivator.

A transcription factor polypeptide is said to be "activated" or "silenced", respectively, when it has been contacted with a ligand that modifies the transcription factor polypeptide so that it is able to stimulate or repress transcription of a gene that is regulated by the particular transcription factor.

A "coactivator" or "transcriptional coactivator," as used herein, includes a polypeptide that is required to mediate transcriptional activation. Coactivators are not required for basal transcription, but rather are involved in stimulation of expression of a gene in response to a signal. Coactivators do not, in their native state, include a DNA binding domain.

A transcription factor, coactivator, or other transcription mediator is said to be involved in modulating expression of a gene in its natural milieu when the transcription mediator modulates expression of the gene in its naturally occurring state. For example, the gene will have the response element (s) and promoter that control expression of the gene as it occurs naturally.

The term "target nucleic acid" refers to a nucleic acid sequence to which a polypeptide or complementary nucleic acid is capable of specifically binding. As used herein, "specifically binding to," when referring to the binding of a polypeptide or complementary nucleic acid to a target nucleic acid, refers to the ability of the polypeptide or complementary nucleic acid to bind to the particular nucleotide sequence under conditions that do not result in appreciable nonspecific binding of the polypeptide to the target nucleic acid. "Subsequence" refers to a sequence of nucleic acids or amino acids that comprise a part of a longer sequence of nucleic acids or amino acids (e.g., polypeptide) respectively.

The term "substantial identity" or "substantial similarity" in the context of a polypeptide indicates that a polypeptides comprises a sequence with at least 70% sequence identity to a reference sequence, or preferably 80%, or more preferably 85% sequence identity to the reference sequence, or most preferably 90% identity over a comparison window of about 10–20 amino acid residues. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

The term "recombinant" when used with reference to a cell indicates that the cell replicates a heterologous nucleic acid, or expresses a peptide or protein encoded by a heterologous nucleic acid. Recombinant cells can express genes that are not found within the native (non-recombinant) form of the cell. Recombinant cells can also express genes found in the native form of the cell wherein the genes are modified and re-introduced into the cell by artificial means.

A "recombinant nucleic acid" comprises or is encoded by one or more nucleic acids which are derived from a nucleic acid which was artificially constructed. For example, the nucleic acid can comprise or be encoded by a cloned nucleic acid formed by joining heterologous nucleic acids as taught, e.g., in Berger and Kimmel, *Guide to Molecular Cloning Techniques, Methods in Enzymology* volume 152 Academic Press, Inc., San Diego, Calif. (Berger) and in Sambrook et al. (1989) *Molecular Cloning—A Laboratory Manual* (2nd ed.) Vol. 1–3 (Sambrook) and in *Current Protocols in Molecular Biology* (Eds. Ausubel et al., Greene Publ. Assoc., Wiley-Interscience, NY, N.Y. (1992). Alternatively, the nucleic acid can be synthesized chemically.

A "heterologous sequence" or a "heterologous nucleic acid", as used herein, is one that originates from a foreign source (or species) or, if from the same source, is modified from its original form. Thus, a heterologous nucleic acid operably linked to a promoter is from a source different from that from which the promoter was derived, or, if from the same source, is modified from its original form. For example, a "heterologous gene encoding a transcription factor" refers to a transcription factor gene that is not normally present in the particular cell. Construction of a heterologous sequence can involve, e.g., treating the DNA with a restriction enzyme to generate a DNA fragment that is capable of being operably linked to the promoter. Modification can occur by techniques such as site-directed mutagenesis.

DESCRIPTION OF THE PREFERRED EMBODIMENTS

The present invention provides methods for modulating expression of a gene or group of genes at the transcriptional level. Also provided are methods for identifying compounds that are capable of modulating expression of a gene of interest. These methods are based upon the discovery that a transcriptional coactivator, when artificially tethered to a DNA binding domain that is specific for a response element, can stimulate or repress expression of a gene under the control of the response element when the tethered coactivator is contacted by a transcription factor. Surprisingly, binding of the transcription factor to DNA directly is not required for modulation of gene expression. Moreover, the degree to which expression of the gene is modulated can greatly exceed that observed when modulation is attempted by increasing the amount of transcription factor that is present. This facilitates the use of the tethered coactivators in highly sensitive assays to identify compounds that are capable of modulating gene expression at the transcriptional level.

A. Tethered Coactivators The tethered coactivators used in the methods of the invention include a DNA binding moiety that is tethered to an activation function derived from a transcriptional coactivator. Transcriptional coactivators, as the term is used herein, are not required for basal transcription and cannot function as transcriptional activators themselves, in part because they lack DNA binding domains. Coactivators are able to mediate transcription induction or repression caused by other polypeptides, such as transcription factors, that are capable of binding DNA. Coactivators from which one can construct a tethered coactivator include, but are not limited to, those of the p160 family and the p300 family. The p160 coactivators, which include SRC-1a and GRIP-1/TIF-2, interact with the ligand binding domain (LBD) of nuclear receptors. The p300 family of coactivators include CBP and the closely related protein p300, which are required for transcriptional activation by CREB, Jun/Fos. Additional coactivators that can be tethered to a DNA binding domain and used in the methods of the invention include those described in, for example, Gill and Tjian (1992) Curr. Op. Genet. Devel. 2: 236–242; Dynlacht et al. (1991) Cell 66: 563–576; Hong et al. (1996) Proc. Nat'l. Acad. Sci. USA 93: 4948–4952; and Janknecht and Hunter (1996) Nature 383: 22–23.

Tethered coactivators that are useful in the methods of the invention can include a full-length coactivator polypeptide, or a smaller portion of the coactivator that includes a domain responsible for coactivator-mediated activation (the "activation function") or repression (the "repression function"). Homologs of coactivators are also useful for constructing tethered coactivators. Active portions of the transcription coactivators that are capable of functional and/or structural interaction with transcription factor polypeptides and other proteins involved in initiation of transcription can be identified using methods described herein. A "portion" of a given coactivator is a peptide that includes at least about twenty, more preferably at least about 40, and more preferably at least about 60 amino acids of the native coactivator polypeptide. To identify additional coactivators and portions of coactivators that are useful in the methods of the invention, one can tether the coactivator of interest, or portion thereof, to a DNA binding domain and assay for the ability of a transcription factor to trigger or repress transcription mediated by the tethered coactivator.

The tethered coactivators include, in addition to a coactivator polypeptide, a DNA binding domain that is capable of specifically binding to a target nucleic acid. The target site is typically located upstream of a gene to be expressed. The target site can be a recognized site at which a transcriptional control agent is capable of binding, or the target site can be chosen based simply on its proximity to the promoter of the gene. Enhancers, which are one example of a target site, are generally found at varying distances upstream of transcription initiation sites. See, e.g., U.S. Pat. No. 5,512,483; Mitchel and Tjian (1989) Science 245: 371; Ptashne and Gann (1990) Nature 346: 329; and Lewin (1990) Cell 61: 1161). In one embodiment, the DNA binding domain is specific for a response element such as that for a hormone, in which case the DNA binding domain will typically include that portion of a receptor protein that binds to hormone response elements (HRE) on the chromatin DNA. The boundaries for these DNA-binding domains have been identified and characterized for the steroid hormone superfamily. See, e.g., Giguere et al. (1986) Cell 46:645–652; Hollenberg et al. (1987) Cell 49:39–46; Green and Chambon (1987) Nature 325:74–78; Miesfield et al. (1987) Science 236:423–427; and Evans (1988) Science 240:889–895. Response elements, including glucocorticoid response elements (GRE) and estrogen response elements (ERE) are also described in, for example, Jantzen et al. (1987) Cell 49: 29; Martinez et al. (1987) EMBO J 6: 3719 and Burch et al. (1988) Mol. Cell. Biol. 8: 1123. For modulating expression of a viral gene, the target nucleic acid can be the binding site for a transcription factor that is involved in regulating transcription of the gene.

While a complete protein can be used as a DNA binding domain, portions of these molecules that are capable of binding to nucleic acids, directly or indirectly, are also useful as DNA binding domains in the chimeric tethered coactivators. To identify such DNA binding domains, one can perform assays such as an electrophoretic mobility shift assay (EMSA) (Scoff et al. (1994) J Biol. Chem. 269: 19848–19858), in which a nucleic acid sequence of interest is allowed to associate with various fragments of a molecule that is capable of binding to the DNA sequence. Association of a portion of the protein with the nucleic acid will result in a retardation of the electrophoretic mobility of the nucleic acid. Another method by which one can identify DNA binding moieties that are suitable for use as guide domains is DNase I footprinting, which is well known to those of skill in the art.

For certain applications, a tethered coactivator will have a DNA binding domain that specifically binds to a target nucleic acid that regulates a gene that is not usually under the control of the particular coactivator. For example, the DNA binding domain from the yeast GAL4 transcription factor can be used to create a chimeric protein that also includes all or an active part of a coactivator that is involved in hormone-regulated transcription (e.g., GAL4 DBD linked to CBP, SRC-1a, or GRIP-1). The DNA binding domain of GAL4 is described in, for example, Carey et al. (1989) J. Mol. Biol. 209: 423–432. One advantage of using a DNA binding domain and corresponding response element that are not normally part of the system in which the coactivator is involved is that the resulting tethered coactivator with a heterologous DNA binding domain permits the analysis of the activation function separately from the DNA binding function.

The DNA binding domain can be either a polypeptide or a nucleic acid. Where the DNA binding domain is a nucleic acid, the nucleic acid will be capable of specifically hybridizing to a target nucleic acid site, such as a response element. Hybridization of the nucleic acid to the target site will place the coactivator polypeptide in a position suitable for activating or repressing expression of a linked gene. An example of an oligonucleotide being chemically linked to a protein by chemical coupling is found in Corey et al. (1989) Biochemistry 28: 8277–8286.

The coactivator domain and the DNA binding domain are tethered together to form a tethered coactivator. For example, a cysteine residue can be placed at either end of a domain so that the domain can be linked by, for example, a sulfide linkage. The modification can be done using either recombinant or chemical methods. More typically, the coactivator domains and DNA binding domains are joined by linker domains, which are typically polypeptide sequences, such as poly glycine sequences of between about 5 and 200 amino acids, with between about 10–100 amino acids being typical. In some embodiments, proline residues are incorporated into the linker to prevent the formation of significant secondary structural elements by the linker. Preferred linkers are often flexible amino acid subsequences which are synthesized as part of a recombinant fusion protein. In one embodiment, the flexible linker is an amino acid subsequence comprising a proline such as Gly(x)-Pro-Gly(x) where x is a number between about 3 and about 100. A linker can also be a single peptide bond, or one or more amino acid residues. In other embodiments, a chemical linker is used to connect synthetically or recombinantly produced coactivator and DNA binding domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The tethered coactivators are conveniently produced by recombinant expression in a host cell. For example, a nucleic acid can encode the tethered coactivator, or either the DNA binding domain or the coactivation domain, can be formed by joining heterologous nucleic acids as taught, e.g., in Berger and Kimmel, *Guide to Molecular Cloning Techniques, Methods in Enzymology* volume 152 Academic Press, Inc., San Diego, Calif. (Berger) and in Sambrook et al. (1989) *Molecular Cloning—A Laboratory Manual* (2nd ed.) Vol. 1–3 (Sambrook). Alternatively, the nucleic acid can be synthesized chemically. The particular procedure used to introduce the nucleic acids into a host cell for expression of the tethered coactivator is not critical. Any of the well known procedures for introducing foreign nucleotide sequences into host cells may be used. These include the use of calcium phosphate transfection, spheroplasts, electroporation, liposomes, microinjection, plasma vectors, viral vectors and any of the other well known methods for introducing cloned genomic DNA, cDNA, synthetic DNA or other foreign genetic material into a host cell (see, Berger, Ausubel and Sambrook, all supra).

B. Modulation of Gene Expression

The invention provides methods for modulating expression of a gene by contacting a response element that is operably linked to the gene with a tethered coactivator. The tethered coactivator is also contacted with an activated transcription factor polypeptide that includes an activation function derived from a transcription factor. The tethered coactivator used in these methods includes a DNA binding domain that is capable of specifically binding to a target DNA sequence in the 5' flanking region of the gene to be expressed, generally a region that is just upstream of the promoter that normally drives expression of the gene. The target DNA sequence may or may not be a response element or other recognized transcriptional control element that is involved in regulating expression of the gene. The DNA binding domain functions to position the coactivator in the promoter/enhancer region of the gene where, upon contact with the transcription factor polypeptide, the coactivator interacts with the basal transcriptional machinery and/or other factor involved in transcription. By choosing as a target site a nucleotide sequence that is present in the 5' flanking regions of each member of a gene family, one can use a single type of tethered coactivator to modulate the expression of multiple genes in the family.

The coactivator polypeptide that is preferred in a particular application can depend in part on which transcription regulation pathway is to be modulated. For example, CBP/p300 and the p160 coactivators, including SRC-1a and GRIP-1 /TIF-2, are useful when a gene of interest is regulated by a nuclear hormone receptor. Tethered coactivators that include a coactivator polypeptide derived from a CBP/p300 coactivator are useful for modulating expression of genes that are regulated by various transcription factors in addition to the nuclear hormone receptors, including the AP-1 transcription factors (e.g., Jun, Fos), Sap-1a, MyoD, and YY1. See, e.g., Janknecht, supra. Genes under the control of virally-encoded transcription factors (e.g., VP 16 of herpesvirus, protein X of hepatitis virus, and the like) can also be modulated using these tethered coactivators.

Where modulation of gene expression is desired in vivo, the tethered coactivator can be administered in its polypeptide form, or it can be expressed within the cell using an expression vector that includes a gene that encodes the tethered coactivator. The gene is operably linked to a promoter that is expressed in the cells of interest. The promoter can be constitutively expressed in the cells, or can be inducible. For example, where a tethered coactivator is desired in cells of a particular tissue, a tissue-specific promoter is used to drive expression of the tethered coactivator gene. Similarly, where it is desired to modulate expression of a gene at a particular stage of development, the tethered coactivator gene can be placed under the control of a developmentally regulated promoter region. Alternatively, the tethered coactivator gene can be placed under the control of a promoter that is inducible by a stimulus that is applied to the cell when expression of the tethered coactivator gene is desired. For example, expression can be turned on by administering a compound that activates the promoter.

Four superclasses of transcription factors from which one can obtain a transcription factor polypeptide are known: the basic domain superclass, the zinc-coordinating DNA binding domain family, the helix-turn-helix superclass, and the P-scaffold superclass (see, e.g., TRANSFAC database, Wingender et al., *Nucleic Acids Res.* 24: 238–241 (1996). For example, the transcription factor polypeptide can be obtained from a member of the leucine zipper class of the "basic domain" subclass, e.g., from a member of the AP-1 family, which includes the jun and fos subfamilies, among others. The Cys4 zinc finger class of the zinc-coordinating DNA binding domain superclass, which includes nuclear hormone receptors, is another example of a suitable source of transcription factor polypeptides. This class includes the steroid hormone receptor family and the thyroid hormone receptor-like family of transcription factors. Nuclear hormone receptors are transcription factors that represent the primary intracellular targets for small lipid soluble ligands such as steroid and thyroid hormones, retinoids, vitamin D3, prostaglandins, and the like. Binding of the hormone or an analog to the hormone receptor can induce transcription of genes that are regulated by response elements for the hormone receptor.

Transcription factor polypeptides will include an activation function derived from a transcription factor. The nuclear receptors, for example, are composed of several conserved domains, as demonstrated by sequence comparison (Krist et al. (1986) *EMBO J* 5: 891) and structure-function analyses (Giguere et al. (1986) *Cell* 46: 645; Kumar et al. (1987) *Cell* 51: 941; Kumar and Chambon (1988) *Cell* 55: 145; and Green and Chambon (1987) *Nature* 325: 75). The DNA binding domain (LBD), which is the most highly conserved domain, is located in the central region and contains a 66–68 amino acid core composed of two zinc fingers. A ligand binding domain (LBD; also referred to as a hormone binding domain (HBD)) is present at the carboxyl terminal, and the amino terminal includes a transcriptional activation domain (AD). This domain, which is less well conserved among the hormone receptors, contains a ligand-inducible transcription initiation function. Activation domains can be defined as polypeptide regions that, when combined with the functional DNA binding domain, increase productive transcription initiation by RNA polymerases. The poorly conserved N-terminal A/B regions of the glucocorticoid and estrogen receptors also contain transcription activating domains. See, Hager and Archer, in *Nuclear Hormone Receptors: Molecu-*

*lar Mechanisms, Cellular functions and Clinical Abnormalities,* (Parker, M. G. ed.), Academic Press Ltd. 217, 1991) and U.S. Pat. No. 5,512,483 for review of nuclear hormone receptors and their structures. In the case of the estrogen receptor, the transcription factor polypeptide can include either or both of AF1 and AF2.

The transcription factor polypeptide which triggers or represses the tethered coactivator can be exogenous or endogenous to the cell; an "exogenous" transcription factor polypeptide refers to one that is not naturally present in the cell, but rather has been added to the cell, either as a polypeptide or as the expression product of a heterologous gene through use of an expression vector. As discussed above for expression of the tethered coactivator, by appropriate choice of a promoter, one can achieve expression of the transcription factor polypeptide when and/or where desired.

The transcription factor polypeptide can be activated for use in the methods of the invention. Activation involves contacting the transcription factor polypeptide with a hormone, or hormone analog for which the transcription factor polypeptide has a hormone binding domain. Other ways to activate transcription factor polypeptides include, for example, the stimulation of phosphorylation cascades (e.g., the MAP kinase or protein kinase A cascades, and the like) by methods known to those of skill in the art, such as administering drugs or peptide hormones (e.g., EGF and the like). The transcription factor polypeptide can be activated prior to, simultaneously with, or after the tethered coactivator binds to the response element. For example, the ER and ERβ can be activated by administering estrogen or an estrogen analog to the receptor. The glucocorticoid receptor can be activated by, for example, treatment with glucocorticoid or a glucocorticoid analog such as dexamethasone.

In one embodiment, contacting the tethered coactivator with a transcription factor polypeptide stimulates expression of the gene. This method is useful, for example, to increase expression of a gene for which a greater level of expression is desirable, such as disease conditions in which a gene is present in a cell but not expressed at all, or not expressed at a sufficient level. For activation of gene expression, a preferred embodiment uses a tethered coactivator derived from a p160- or CBP/p300-family coactivator and the corresponding transcription factor polypeptide is derived from an estrogen receptor (ER), an estrogen-β (ERβ) receptor, or an AP-1 transcription factor such as jun or fos.

In another embodiment, the methods of the invention are useful for repressing expression of a gene. This method is useful in situations where expression of a particular gene is undesirable, such as diseases that involve overexpression of a gene, or expression of a particular gene at an inappropriate time. For repression of gene expression, a preferred embodiment uses a tethered CBP coactivator and an activated transcription factor polypeptide derived from a glucocorticoid receptor. Administration of an activated glucocorticoid receptor polypeptide to a cell that contains a CBP coactivator tethered to a DNA binding domain can repress the ability of the estrogen receptor and estrogen to stimulate transcription of the gene.

These methods are useful, for example, to stimulate or repress transcription of cellular or viral genes. For treating a human or other animal, the tethered coactivator and, if needed, exogenous transcription factor, can be administered as polypeptides by methods known to those of skill in the art. For example, the polypeptide(s) can be formulated as pharmaceutical compositions that are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the tethered coactivator polypeptides and transcription factor polypeptides, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

In another embodiment, the compositions are useful for parenteral administration, such as intravenous administration or administration into a body cavity or lumen of an organ. The compositions for administration will commonly comprise a solution of the tethered coactivator with or without transcription factor polypeptide dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The pharmaceutical compositions can also contain an agent that can activate the transcription factor polypeptide; alternatively, the activating agent can be administered separately. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of tethered coactivator in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the tethered coactivators, or a cocktail thereof (i.e., with other proteins such as a transcription factor polypeptide), can be administered for therapeutic treatments. In therapeutic applications, compositions are administered to a patient suffering from a disease or other condition characterized by underexpression or overexpression of a particular gene or group of genes in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the proteins of this invention to effectively treat the patient.

Gene therapy can also be used to introduce nucleic acids that encode the tethered coactivator and the transcription factor. Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies. As an example, in vivo expression of cholesterol-regulating genes, genes which selectively block the replication of HIV, and tumor-suppressing genes in human patients dramatically improves the treatment of heart disease, AIDS, and cancer, respectively. For a review of gene therapy procedures, see Anderson, *Science* (1992) 256:808–813; Nabel and Felgner (1993) *TIBTECH* 11: 211–217; Mitani and Caskey (1993) *TIBTECH* 11: 162–166; Mulligan (1993) *Science* 926–932; Dillon (1993) *TIBTECH* 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al. (1995) in *Current Topics in Microbiology and Immunology* Doerfler and Böhm (eds) Springer-Verlag, Heidelberg Germany; and Yu et al., *Gene Therapy* (1994) 1:13–26.

Delivery of the gene or genetic material into the cell is the first critical step in gene therapy treatment of disease. A large number of delivery methods are well known to those of skill in the art. Such methods include, for example, delivery of naked DNA by injection or by use of a particle bombardment device (Felgner, U.S. Pat. No. 5,580,859), liposome-based gene delivery (Debs and Zhu (1993) WO 93/24640; Mannino and Gould-Fogerite (1988) BioTechniques 6(7): 682–691; Rose U.S. Pat No. 5,279,833; Brigham (1991) WO 91/06309; and Felgner et al. (1987) *Proc. Natl. Acad. Sci. USA* 84: 7413–7414), and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4:43, and Cometta et al. *Hum. Gene Ther.* 2:215 (1991)). Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al. (1992) *J Virol.* 66(5) 2731–2739; Johann et al. (1992) *J Virol.* 66 (5):1635–1640 (1992); Sommerfelt et al., (1990) *Virol.* 176:58–59; Wilson et al. (1989) *J. Virol.* 63:2374–2378; Miller et al., *J Virol.* 65:2220–2224 (1991); Wong-Staal et al., PCT/US94/05700, and Rosenburg and Fauci (1993) in *Fundamental Immunology*, Third Edition Paul (ed) Raven Press, Ltd., New York and the references therein, and Yu et al., *Gene Therapy* (1994) supra).

Adenovirus-based vectors are also used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors. Construction of recombinant AAV vectors are described in a number of publications, including Lebkowski, U.S. Pat. No. 5,173,414; Tratschin et al. (1985) *Mol. Cell. Biol* 5(11):3251–3260; Tratschin, et al. (1984) *Mol. Cell. Biol.*, 4:2072–2081; Hermonat and Muzyczka (1984) *Proc. Natl. Acad. Sci. USA*, 81:6466–6470; McLaughlin et al. (1988) and Samulski et al. (1989) *J. Virol.*, 63:03822–3828. Cell lines that can be transformed by rAAV include those described in Lebkowski et al. (1988) *Mol. Cell. Biol.*, 8:3988–3996.

The invention also provides methods for identifying previously unknown coactivators that are involved in nuclear receptor-mediated transcriptional regulation. An expression library of cDNA molecules is prepared from mRNA obtained from a cell in which a gene of interest is expressed. Expression screening is described in, for example, Ausubel, supra. The expression vector used for the library includes a DNA binding domain coding region adjacent to the insertion site for the cDNA clones. The expression library DNAs are co-introduced into a host cell with a transcription factor polypeptide, which can also be provided by means of expression of a heterologous gene. A hormone or analog that binds to the transcription factor polypeptide is also introduced into the cells, thus activating the transcription factor polypeptide. In a preferred embodiment, the host cells also contain a reporter gene that is operably linked to a response element that corresponds to the DNA binding domain encoded by the expression vector. Clones that encode an activation domain of a coactivator will trigger expression of genes that are operably linked to the response element.

C. High Throughput Assays for Transcription-modulating Compounds

The invention also provides methods and compositions for identifying agents that are useful in modulating gene transcription. These agents are useful in diagnosing and treating disease conditions that are characterized by undesirable transcription of one or more genes, or a lack of desirable transcription. Such diseases include microbial, fungal and viral infections, cancer, inflammatory diseases, cancer, immune diseases, and the like. The methods of the invention provide assays for rapidly identifying test compounds that are capable of modulating transcription of a gene of interest.

The assays provided by the invention for identifying transcription-modulating compounds involve contacting a reporter gene that is under the control of a response element located upstream of a promoter sequence with a tethered coactivator and a transcription factor polypeptide. The transcription factor polypeptide is contacted with the test compound, generally prior to contacting the transcription factor polypeptide with the tethered coactivator and the response element. Expression of the reporter gene is detected to determine whether transcription is increased, decreased, or unchanged, compared to a control.

In one embodiment, the transcription factor polypeptide is derived from a transcription factor that is involved in modulating expression of the gene of interest in its natural milieu. Thus, a test compound that affects the ability of the transcription factor to trigger or repress transcription mediated by the tethered coactivator will likely have the same effect on transcription of the gene in vivo.

To determine whether a particular compound has an effect on transcription in these assays, a reporter gene is conveniently used. The reporter gene will typically include a minimal promoter sequence operably linked to a structural gene for which the gene product is readily detected when present. A minimal promoter refers to, for example, a TATA box and an initiator element containing a transcriptional initiation site (Smale and Baltimore (1989) *Cell* 57: 103) located about 20 to 50 bases downstream from the TATA box. Typically, no other upstream elements are provided. The minimal promoter can be of mammalian or viral origin.

Conveniently, the minimal promoter is present in a vector that includes restriction endonuclease cleavage sites upstream of the promoter for insertion of a response element, and downstream of the promoter for insertion of the reporter structural gene. A variety of reporter gene plasmid systems are known, such as the common chloramphenicol acetyltransferase (CAT) and β-galactosidase (e.g., bacterial lacZ gene) reporter systems, the firefly luciferase gene (See, e.g., Cara et al. (1996) *J. Biol. Chem.* 271: 5393–5397), the green fluorescence protein (see, e.g., Chalfie et al. (1994) *Science* 263: 802) and many others. Selectable markers which facilitate cloning of the vectors of the invention are optionally included. Sambrook and Ausubel, both supra, provide an overview of selectable markers.

These assays are typically performed in vivo, with the transcription factor polypeptide and the tethered coactivator produced in the cell from one or more expression vectors. A vector that carries the reporter gene can also be transfected into appropriate host cells. Alternatively, the transcription factor polypeptide and the tethered coactivator can be transferred into the host cell as polypeptides by methods known to those of skill in the art. The transcription factor polypeptide can be activated (or silenced) by contact with an agent appropriate for the particular transcription factor polypeptide. The test compound is prior to, simultaneous with, or after, contact with the test compound. Expression of the reporter gene is detected to determine whether the compound inhibits the ability of activated transcription factor polypeptide to stimulate transcription, or overcomes the repressive effect of an inactivated transcription factor polypeptide.

The particular cells used in the screening assays are not critical, so long as the cells contain the additional transcriptional components, including the basal transcription machinery (BTM) that are required for transcription. For example, eukaryotic cells including yeast, insect, and mammalian cells are suitable as host cells.

Of particular interest are compounds that block the stimulation of transcription of genes involved in disease. For example, overexpression of genes regulated by estrogen and the estrogen receptor has been linked to breast cancer. Similarly, compounds that are able to block coactivator-mediated expression of pathogen genes, including viral genes, could provide an effective treatment for illness caused by the pathogen. Such genes for which the invention provides a screening method for inhibitors include those under the control of a viral promoter, such as an HIV-1 or HIV-2 LTRs, HTLV-LTRs, a Herpes virus tk promoter, a vaccinia promoter, a pox virus promoter, a flu virus promoter, an adenovirus promoter, etc. The screening methods are also useful for identifying compounds that are capable of modulating transcription of oncogenes, including viral oncogenes such as the E7 gene of human papillomavirus and the E1A gene of adenovirus, as well as cellular oncogenes such as Rb, E2F, myc, abl, and the like. Preferred test compounds modulate, preferably disrupt, interaction between the tethered coactivator and the transcription factor polypeptide, or between a transcription factor polypeptide and its cognate ligand.

The invention also provides a method for identifying compounds that "mimic" hormones and other ligands insofar as their effect on transcription. For example, tamoxifen and related antiestrogens, which are used to treat hormone-dependent breast cancer, bind to the ER and block its activation by estrogen. However, tamoxifen has the undesirable side effect of activating, rather than repressing, estrogen-regulated genes in certain types of cells such as uterine cells. Webb et al., *Mol. Endocrinol.* 9: 443–456. The transcription factors jun and fos, which bind to AP1 DNA sequences, also bind to the coactivator CBP. The inventors demonstrated that estrogen and the estrogen receptor can trigger jun/fos-bound CBP to stimulate transcription of genes regulated by AP1 sites. Surprisingly, binding of the ER to an ER response element is not required for this activity.

This discovery makes possible a method for screening a test compound for the ability to modulate this so-called "indirect" estrogen response. The method involves providing a cell that includes an activated estrogen receptor and a reporter gene under the control of a promoter and an AP1 site. The cell is contacted with a chimeric protein that comprises a DNA binding moiety that is capable of specifically binding to the AP1 site and a polypeptide that comprises an activation function derived from a transcriptional coactivator. The cell is contacted with the test compound, prior to, simultaneously with, or after contacting with the chimeric protein. Expression of the reporter gene is detected. If expression is decreased in the presence of a test compound, the compound reduces the indirect estrogen response.

Other compounds that are believed to mimic estrogen may also cause undesired stimulation of estrogen-regulated genes. Identification of such compounds can be difficult because the compounds sometimes bear little structural resemblance to estrogen. The invention provides a simple means for assaying whether a particular compound does in fact stimulate transcription of estrogen-regulated genes.

EXAMPLES

The following examples are offered to illustrate, but not to limit the present invention.

Example 1

Estrogen Receptor Triggers Expression Mediated by Tethered p160-CBP Coactivator Complex A. Materials and Methods 1. Plasmids.

A reporter gene was constructed by placing a luciferase structural gene under the control of the adenovirus E1b minimal promoter. Five GAL4 17-mer response elements were placed upstream of the E1b promoter. For the purposes of these studies, the vector backbone was modified to remove an AP-1 site naturally present in pUC (Kushner et al., *Mol Endocrinol* 8: 405–7 (1994)).

A gene encoding a fusion protein derived from the estrogen receptor (ER) (E-GAL-E, FIG. 3B) in which the GAL4 DNA binding domain (GAL4-DBD) replaced the estrogen receptor DNA binding domain (ER-DBD). E-GAL-E was constructed by standard splicing by overlap extension PCR techniques and contains sequences for ER-AB (amino acids 1–184), the GAL4-DBD (amino acids 1–147) and the ER hinge/LBD (amino acids 250–595). Expression vectors for the wild type ER-LBD and the ER-LBD AF2 mutant were constructed by site-directed mutagenesis using the vector HE-14 (Chambon). All other ER expression vectors were previously described in Webb et al., *Mol. Endocrinol.* 9: 443–456 (1995).

A CMV-driven expression vector for SRC-1a (amino acids 1–1462) and GAL-SRC-1a was also prepared. Full length GRIP-1-1 cDNA was isolated from a yeast expression vector as an EcoRI fragment and recloned into the SV40-driven expression vector SG5. GAL4-CBP fusions were previously described (Swope et al., *J. Biol. Chem.* 271:

28138–45 (1996); Kwok et al., *Nature* 370: 223–6 (1994)). The CBP full length expression vector was as described by Kamei et al., *Cell* 85: 403–14 (1996).

Glutathione-S-transferase (GST)-fusion proteins for mouse ER-LBD (amino acids 313–599) and the ER-LBD-AF2 mutant (converting amino acids 547 and 548 from methionine and leucine, respectively, to alanine) and GST-AB have been described (Webb et al., supra.; Cavailles et al. *EMBO J:* 14: 3741–51 (1995)). GST-CBP fusion proteins were previously described by Yang et al., *Nature* 382: 319–24 (1996). The amino-terminal CBP protein was produced by cloning a full length CBP cDNA into SG5 as a BamHI fragment. As previously shown, this produces a protein of about 170 Kd that contains the amino-terminal two thirds of the CBP molecule (Chakravarti et al., *Nature* 383: 99–103 (1996)). In vitro translated CBP C-terminal expression vector (1678–2441) was previously described (Kwok et al., *Nature* 370: 223–6 (1994)).

2. Transfections.

HeLa cells were transfected as described in Webb et al., supra. Transfections included 5 μg of the GAL4 responsive reporter gene, 1 μg of GAL4-DBD/coactivator expression vectors, 1 μg of pJ3-b-GAL vector for normalization of transfection efficiency, 5 μg of ER and 5 μg of native coactivator expression vectors. Where noted, transfections utilized 3 μg of jun or fos expression vectors. Estrogen was added to a final concentration of 100 nM and tamoxifen to 5 μM.

3. In Vitro Binding Assays.

In vitro binding assays were performed as previously described in Webb et al., supra.

B. Results and Discussion

Prior to the experiments described herein, a hypothetical model proposed that coactivators act as bridges between a DNA bound transcription factor and the basal transcription machinery (BTM). This model implied that once the coactivator is recruited to a promoter, the transcription factor becomes dispensable and the coactivator should be able to activate transcription in its own right. To test this idea we compared the ability of the ER-LBD and its coactivators to activate transcription when tethered directly to DNA (FIG. 1A). Whereas the ER-LBD, fused to the yeast GAL4 DNA binding domain (GAL-LBD), efficiently activated a GAL4 responsive target promoter in the presence of estrogen, neither GAL-SRC-1a nor GAL-CBP was able to induce transcription. Overexpression of combinations of coactivators, either free or as GAL4 fusion proteins, also failed to activate GAL4 responsive transcription. This is consistent with previous results which show that both SRC-1a and CBP (Swope et al., Kwok et al., both supra.) possess strong latent transactivation functions, but only activate transcription weakly in their full length form. Free SRC-1a, GRIP-1 and CBP were able to potentiate the transcriptional activity of the ER-LBD. Thus, SRC-1a and CBP participate in transcriptional activation by the ER-LBD, yet are not sufficient to mediate transcription when recruited directly to a promoter.

One explanation for the apparently paradoxical behavior of the ER coactivators is that ER contact could be required to trigger the activity of the p160-CBP complex. To test this hypothesis, we reversed the usual configuration of the transcription factor and coactivator at a promoter. We examined whether ER, in the absence of its cognate DNA binding site, would potentiate the activity of either the p160s or CBP when the coactivator was tethered to DNA. FIG. 1B shows that a GAL4-SRC-1a fusion protein activated transcription only weakly in the absence of estrogen, but strongly either in the presence of estrogen or the mixed agonist/antagonist tamoxifen. ER was also able to potentiate the modest activity of a GAL4 fusion to GRIP-1 and the activity of GAL-CBP. Both estrogen and tamoxifen failed to induce promoter activity when the isolated GAL4-DBD was used as an activator, or when ER was omitted from the transfection. ER also failed to potentiate other transcriptionally active GAL4 fusion proteins, such as GAL4-SP1. ER is therefore specifically able to potentiate the transcriptional activity of its coactivators, SRC-1a, GRIP-1 and CBP.

Since the p160s are known to interact with CBP in vivo, we asked whether either SRC-1a or GRIP-1 might be involved in ER action at GAL-CBP. We first examined whether overexpression of the p160s would affect ER action at CBP. FIG. 2A shows that transfected SRC-1a and GRIP-1 both potentiated tamoxifen and estrogen action at GAL-CBP. A shorter version of GRIP-1 (amino acids 322–1141), that acts as a dominant negative inhibitor of nuclear receptor action (Hong et al., supra.), inhibited ER action at CBP. Overexpression of CBP (or p300, not shown) also reduced ER dependent activation of GAL-CBP by about 70%. This was unlikely to be due to non-specific effects upon transcription, because overexpression of CBP enhanced the activity of the GAL4 /ER-LBD fusion protein (FIG. 1A), and was more likely to be due to titration of a limiting coactivator. Thus, ER action at GAL4-CBP is specifically enhanced by SRC-1a and GRIP-1, suggesting that the p160s are involved in ER potentiation of CBP activity.

Figure 2B:
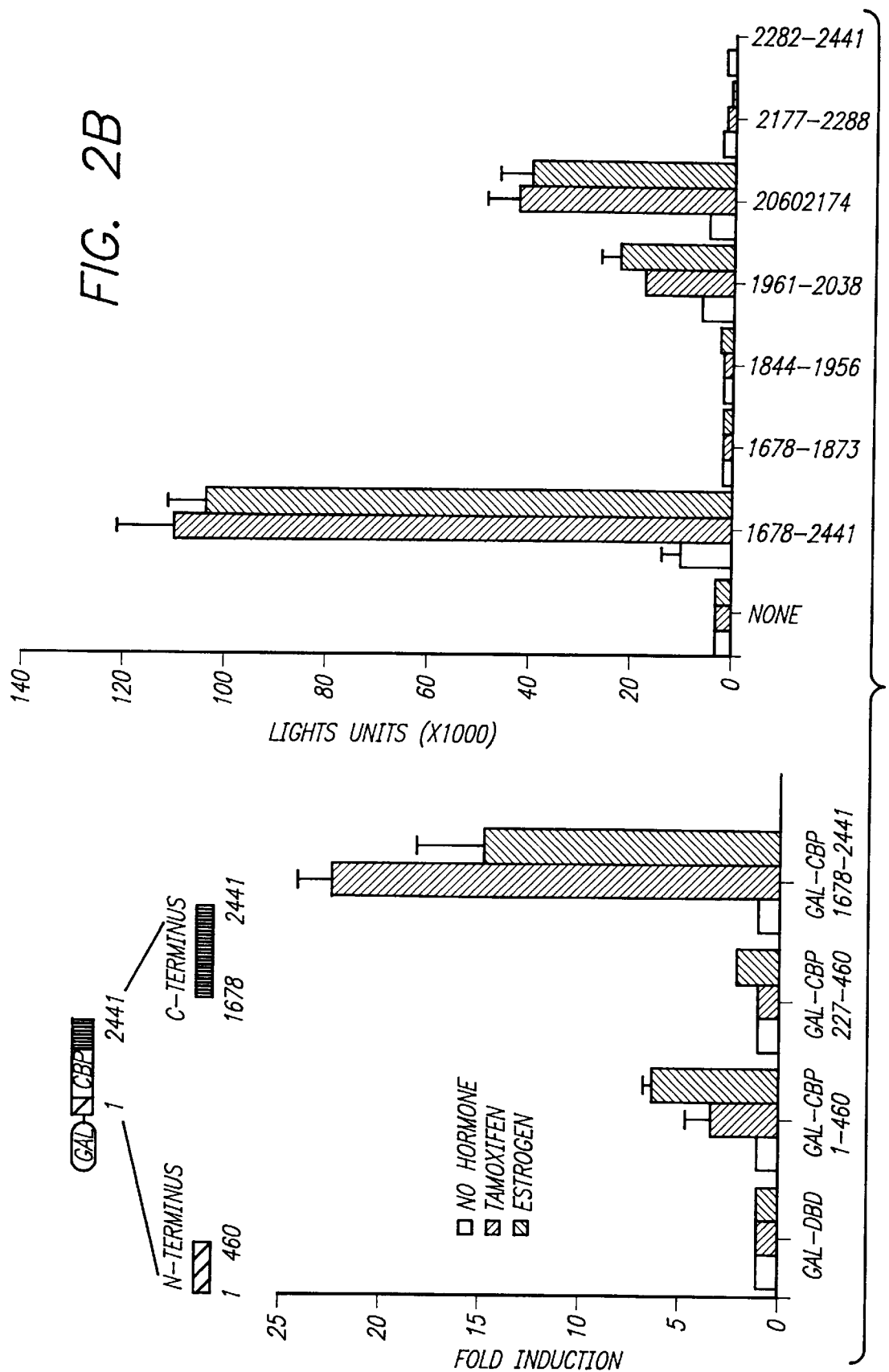

We next examined whether ER regulation of CBP activity mapped to the region within the CBP carboxy-terminus that has been implicated in SRC-1 a binding (FIG. 2B). ER was able to strongly potentiate the activity of the carboxy-terminal domain (amino acids 1678–2441) fused to GAL4. In contrast, the remaining parts of CBP showed, at most, modest response to ER ligands. Further mapping within the CBP C-terminus revealed that the strongest ER regulation of transcriptional activity was obtained with a fragment of CBP that spanned amino acids 2060–2174. This coincides with the location of the latent CBP carboxy-terminal activation function (Swope et al., supra.) and also the site for SRC-1a (Kamei et al., supra.) and GRIP-1 binding (see below). The fact that the site of ER action on CBP maps to the site of p160 binding is consistent with a role for p160s in ER regulation of CBP activity.

Figure 3A:
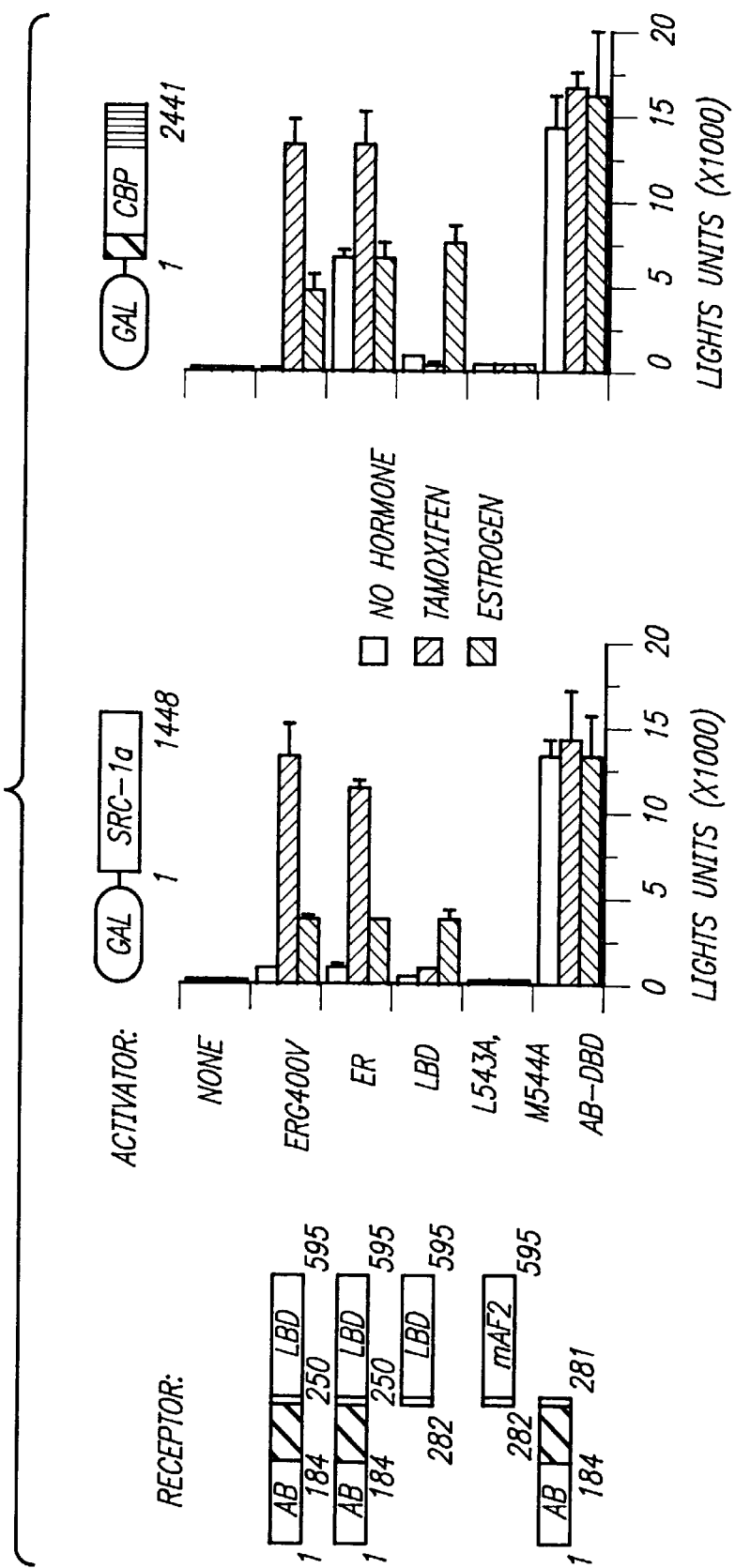
FIGS. 3A–3B present data which demonstrate that ER trans-activation functions are needed to potentiate coactivators.

The ER, like other nuclear receptors, possesses a carboxy-terminal LBD, that contains the strong ligand induced transcriptional activation function AF2, a centrally located DBD, and an amino terminal (AB) domain, that contains the weak constitutive activation function AF1 (Tora et al., *Cell* 59: 477–87 (1989); Berry et al., *EMBO J* 9: 2811–2818 (1990); Kumar et al., *Cell* 51: 941–951 (1987); and Lees et al., *Nucl. Acids Res.* 17: 5477–5488 (1989)). We tested whether these conventional trans-activation functions were required for ER potentiation of SRC-1a and CBP activity (FIG. 3A). Remarkably, the isolated ER-LBD potentiated the activity of both coactivators in an estrogen dependent manner, even in the absence of the ER-DBD. A mutation that disrupted AF2 (L543, M544A) abolished estrogen dependent activation. Thus, AF2 is necessary for the LBD to mediate an estrogen response at both SRC-1a and CBP. The ER AB-DBD region also strongly potentiated the activity of GAL-SRC-1a and GAL-CBP, to levels that were similar to those obtained with tamoxifen-liganded ER. Deletion of the AB domain abolished both constitutive activation by the AB-DBD region and tamoxifen activation by full length ER (not shown). Thus, AF1, which resides in the AB domain, activates both tethered SRC-1a and CBP. We conclude that ER action at coactivators, like ER action at classical estrogen response elements, involves AF1 and AF2.

Figure 3B:
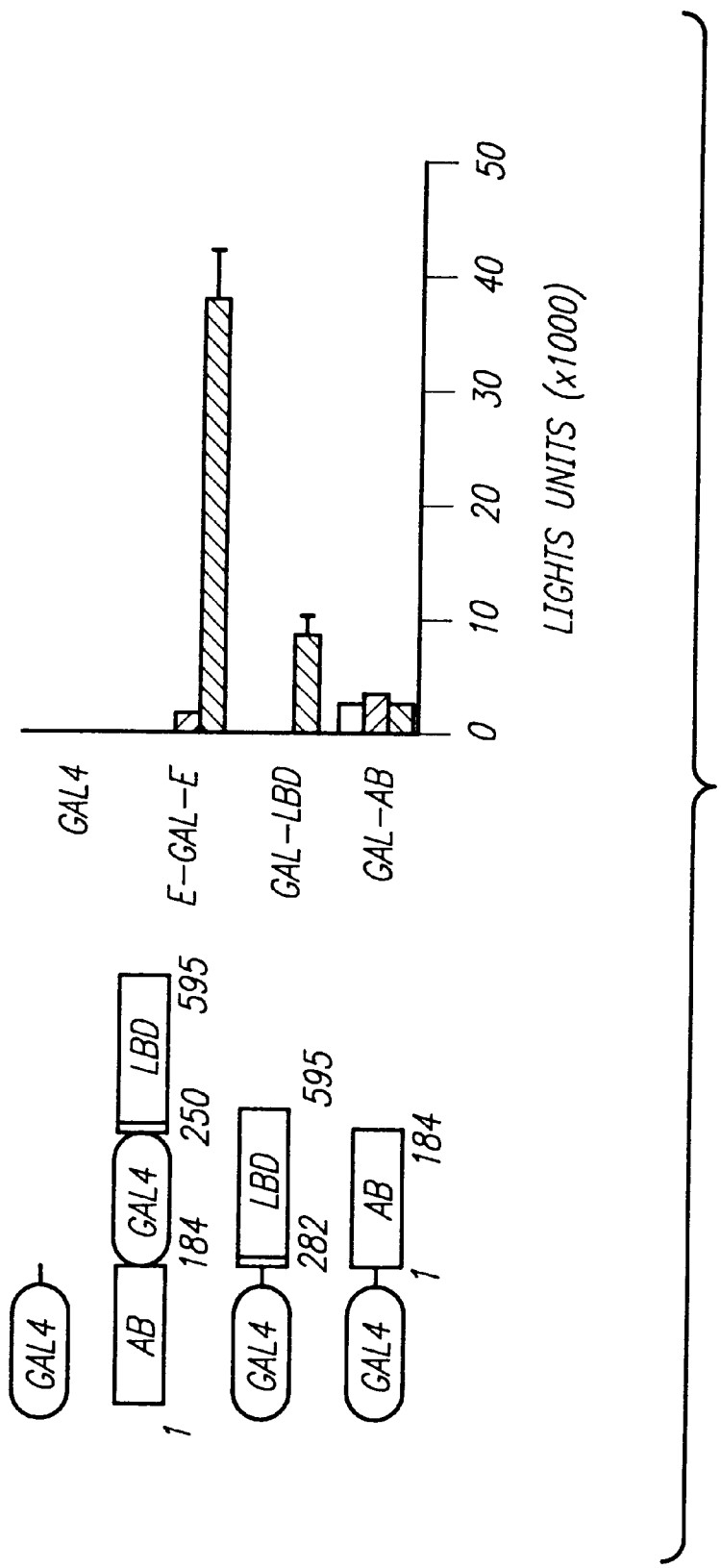

Because AF1 is generally weak when ER is bound to DNA, yet is strong in potentiating tethered coactivators, we confirmed that AF1 and AF2 behaved normally when directly recruited to the GAL4 responsive promoter in the context of an ER fusion in which the GAL4-DBD replaced the ER-DBD (E-GAL-E, FIG. 3B). Thus, AF1 is weak when it is bound to DNA, but strong in potentiation of tethered coactivators, even in the context of the same promoter. The relative strength of AF1 in activation of tethered co-activators explains why tamoxifen-liganded ER, whose activity reflects AF1 (Berry et al., supra.), strongly activates both SRC-1a and CBP.

We next examined whether the two biologically active regions of the ER molecule, the LBD and AB domain, were capable of binding either the p160s or CBP in vitro. As expected, the ER-LBD interacted with both SRC-1a and GRIP-1 in an estrogen dependent, AF2 sensitive manner (FIG. 4A). Unlike other nuclear receptors (Kamei et al., Chakravarti et al., both supra.), the ER-LBD failed to bind the CBP amino-terminus. The LBD did bind the carboxy-terminus of CBP, but weakly and in a ligand- and AF2-independent manner. Thus, the ER-LBD binds p160s, and not CBP, in a manner that parallels the estrogen and AF2 dependent ability of the ER-LBD to stimulate tethered coactivators (FIG. 3A).

Since AF1 was able to potentiate SRC-1a and CBP action, we examined whether the AB domain, which contains AF1, might also interact with members of the coactivator complex (FIG. 4A). The ER-AB domain bound to both SRC-1a and GRIP-1, although less strongly than the LBD. The AB domain did not interact with either the CBP amino-terminus or the CBP carboxy-terminus. Thus, both ER activation functions, AF1 and AF2, have the potential to functionally interact with the coactivator complex by binding p160 proteins.

We next mapped the relative positions of binding sites for both the p160s and ER within the CBP carboxy-terminus. FIG. 4B shows that SRC-1a interacted mainly with a fragment (D) that stretched from amino acids 2041–2240, consistent with other reports that have placed the SRC-1a binding site within this region (Kamei et al., supra.). GRIP-1 also interacted with this fragment of CBP, albeit more strongly than SRC-1a. In contrast, the ER specifically bound to two fragments of the CBP C-terminus that stretched from amino acids 1678–2000 (A and B) and overlapped only from amino acids 1801–1880. Neither SRC-1a, GRIP-1 nor ER interacted with the amino terminal portion of CBP (data not shown). Thus, the region of the CBP C-terminus that is most strongly affected by ER (FIG. 2C) binds SRC-1a and GRIP-1, but not ER. We infer that ER interactions with endogenous p160s underlie ER's ability to activate tethered CBP as shown in FIG. 2A. This points to a central role for ER/p160 contacts in potentiation of coactivator function.

Figure 5A:
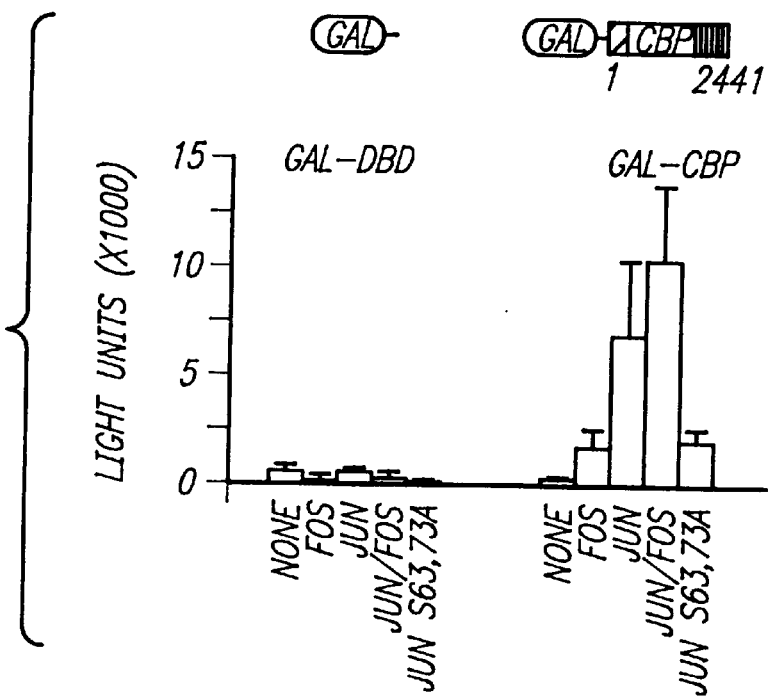
FIGS. 5A–5B demonstrate that the AP-1 proteins Jun and Fos potentiate CBP activity.
Figure 5B:
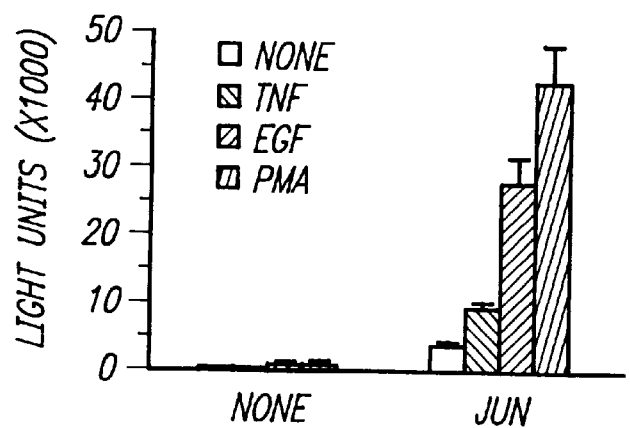

To examine whether other transcription factors might also potentiate coactivator function, we tested whether the AP-1 proteins Jun and Fos, which both bind CBP (Arias et al., Nature 370: 226–229 (1994); Bannister et al., Oncogene 11: 2509–2514 (1995); Bannister et al, EMBO J 14: 4758–4762 (1995), were able to regulate CBP action. FIG. 5A shows that both Jun and Jun/Fos potentiated the activity of full length CBP. The ability of AP-1 proteins to activate CBP depends upon transcriptional activation functions because a mutation (ser63,73 ala) that reduces Jun transcriptional activity also reduced the ability of Jun to potentiate CBP activity (Bannister et al., Oncogene, supra.). Jun activation of full length CBP was also further induced by treatments with TNFα, EGF or PMA, each of which enhances the activity of the c-Jun transactivation function through a mechanism that requires CBP contact (Arias et al., Bannister et al., supra.). The fact that two disparate types of transcription factors, the ER and Jun/Fos, can potentiate the activity of their coactivator proteins suggests that the ability of transcription factors to regulate coactivators may be widespread.

In summary, we propose that when transcription factors, such as ER, are bound to DNA they interact with coactivators in two steps (FIG. 6A). First, ER recruits the co-activator complex. Second, in a hitherto unrecognized step, the ER triggers the activity of coactivator complex. When the coactivator is artificially tethered to DNA, bypassing the role of ER in recruitment, the role of ER in triggering is revealed (FIG. 6B). While our work does not address how ER can trigger the activity of the co-activator complex, in principle, ER could employ separate contacts with basal transcription factors to stabilize the general transcription machinery at the promoter, help the coactivator complex assemble, or convert individual coactivators from an inactive to an active state. Independent lines of evidence also argue that activators have separate recruitment and triggering functions for transcription. For example, the activator CREB binds CBP upon stimulation with cyclic AMP, but one mutation in the activation domain, Ser142Asp, that allows normal cyclic AMP induced binding of the CREB activation function to CBP, nonetheless abolishes transcriptional activation (Sun & Maurer, J. Biol. Chem. 270: 7041–7044 (1995)). This is consistent with the idea that the CREB mutant is proficient for recruiting, but not triggering. Similarly, when the ER AB-DBD region is bound to DNA, the free LBD can further stimulate transcription in the presence of estrogen (McInerney et al., Proc. Nat'l. Acad. Sci. USA 93: 10069–10073 (1996); Kraus et al., Proc. Nat'l. Acad. Sci. USA 92: 12314–12318 (1995)). This surprising result can be explained by the notion that the AB-DBD region would recruit the coactivator complex, and the free LBD is able to trigger it.

The fact that ER can trigger coactivators, such as CBP, that are artificially pre-recruited to DNA (FIG. 6B) also implies that ER could trigger CBP that has been prerecruited by other transcription factors. In additional experiments that we performed, ER, which stimulates AP-1 activity (Gaub et al., Cell 63: 1267–1276; Webb et al., Mol. Endocrinol. 9: 443–456 (1995); Umayahara et al., J. Biol. Chem. 269: 16433–16442 (1994) and Philips et al., J. Biol. Chem. 268: 14103–14108 (1993)), enhanced the activity of CBP that is tethered to the activation functions of Jun, Fos and Elk-1. Thus, in addition to the well known classical pathway in which ER binds to DNA and recruits coactivators to stimulate gene expression, ER has widespread potential to regulate gene expression through transcription factors that utilize CBP as a coactivator.

Finally, when ER binds DNA (FIG. 6A), the combined process of recruitment and triggering requires the synergistic activity of AF1 and AF2, neither of which works well in isolation (Tora et al., Berry et al., Kumar et al., Lees et al., and McInerney et al., all supra., and Danielian et al., EMBO J. 11: 1025–1033 (1992) (see also FIG. 3B). In contrast, when the coactivator complex is pre-recruited to DNA (FIG. 6B), ER dependent triggering requires either AF1 or AF2, which function independently and strongly (FIG. 3). Consequently, tamoxifen, whose activity reflects isolated AF1, strongly triggers prerecruited coactivator complexes. It is well established that tamoxifen shows diverse and puzzling estrogen-like effects on gene expression in vivo (Webb et al., supra.; Norris et al., *Molecular Endocrinology* 10: 1605–1616 (1996)). Our results suggest that many of these instances of tamoxifen agonism will prove to arise from ER dependent triggering of genes with pre-recruited coactivator complexes.

C. Summary of Conclusions

The estrogen receptor (ER) activates gene expression by a mechanism that requires coactivators of the p160 family and CBP/p300 (Onate et al., Kamnei et al., Hong et al., Chakravarti et al., and Hanstein et al., all supra., and Voegel et al., *EMBO J.* 15: 3667–3675 (1996); Smith et al., *Proc. Nat'l. Acad. Sci. USA* 93: 8884–8888 (1996)). Previous models to explain the function of coactivators suggested that coactivators work as bridges between DNA bound transcription factors and the basal transcription machinery (BTM) (Janknecht and Hunter, *Nature* 383: 22–23 (1996)). This model implied that the steroid receptor acts as an inert platform for coactivator recruitment, and that coactivators are the true effector of gene expression. Here, we show that SRC-1a and CBP do not activate transcription efficiently when tethered directly to DNA in the absence of receptor. Supplying ER, however, enhances the ability of both coactivators to activate transcription, even in the absence of ER DNA binding. The AP-1 proteins Jun and Fos also increase the activity of their coactivator CBP. Thus, coactivators need transcription factors to activate gene expression. Our results demonstrate that transcription factors recruit coactivators to the promoter, then trigger the subsequent activity of the coactivator complex.

Example 2

Glucocorticoid Receptor Represses CBP-mediated Estrogen-stimulated Transcription This Example demonstrates the effect of the human glucocorticoid receptor on the ability of estrogen and the estrogen receptor to stimulate transcription mediated by a CBP coactivator polypeptide tethered to a GAL4 DNA binding domain. These experiments utilized a reporter gene that consisted of five binding sites for the yeast protein GAL4 just upstream of a minimal promoter (TATA box) driving expression of a luciferase structural gene. The reporter gene was transfected into HeLa cells along with expression vectors for a fusion of the GAL4 DNA binding domain to the carboxyl-terminus of CBP (amino acids 1678–2441), for the human estrogen receptor, and for the human glucocorticoid receptor.

Figure 7:
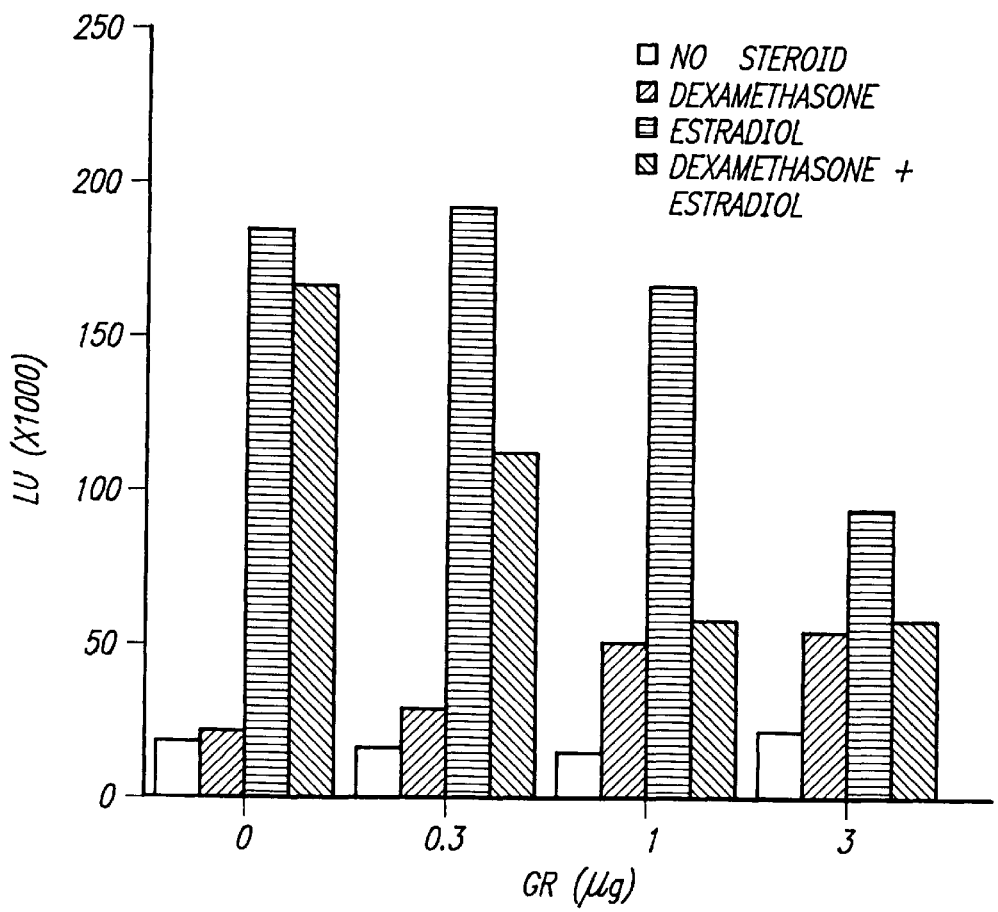
FIG. 7 presents data which demonstrate that dexamethasone activates the glucocorticoid receptor to repress transcription stimulated by tethered CBP preactivated by estrogen and its receptor.

The results of this experiment, which are shown in FIG. 7, demonstrate that the presence of estrogen (estradiol) stimulates expression of the reporter gene. This stimulation is inhibited by the presence of dexamethasone, a synthetic glucocorticoid agonist. The repression is a function of the amount of glucocorticoid receptor transfected. Some repression occurred due to the endogenous glucocorticoid receptor found in HeLa cells.

Figure 8:
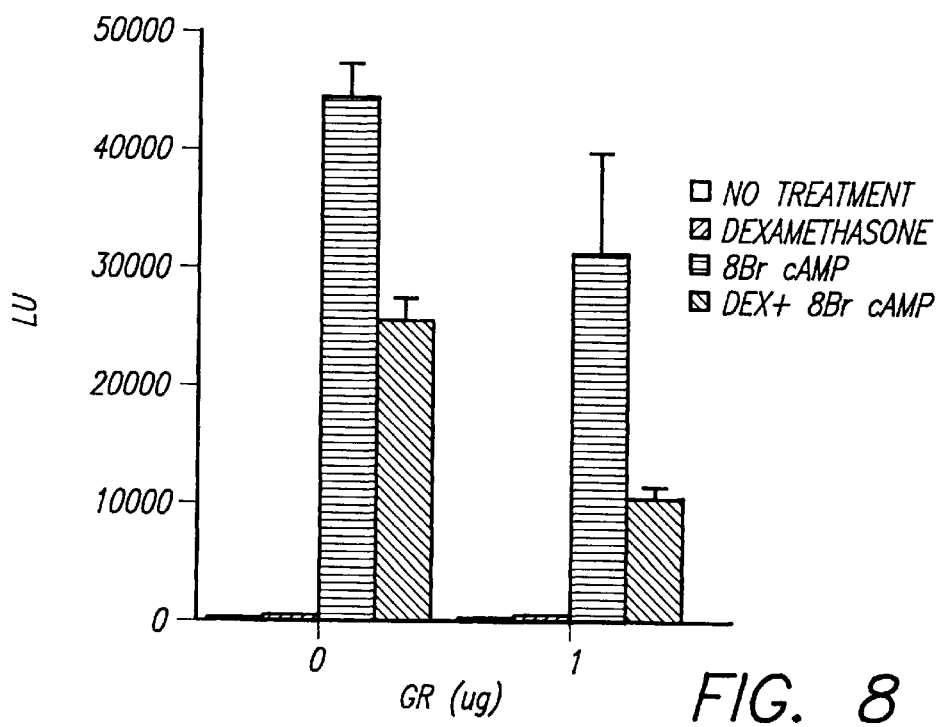
FIG. 8 presents data which demonstrate that dexamethasone inhibits transcription stimulated by 8-bromo cyclic AMP and GAL-CBP in GT1 cells.

In an additional experiment, the reporter gene was transfected into GT1 cells, a hypothalamic cell line, along with expression vectors for a fusion of the GAL4 DNA binding domain to full length CBP, for the human estrogen receptor, and for the human glucocorticoid receptor. As shown in FIG. 8, when the reporter gene was preactivated by treatment with cyclic AMP, the synthetic glucocorticoid dexamethasone repressed gene expression. In this instance, the endogenous glucocorticoid receptors in GT1 cells were sufficient for repression.

Example 3

Figure 9:
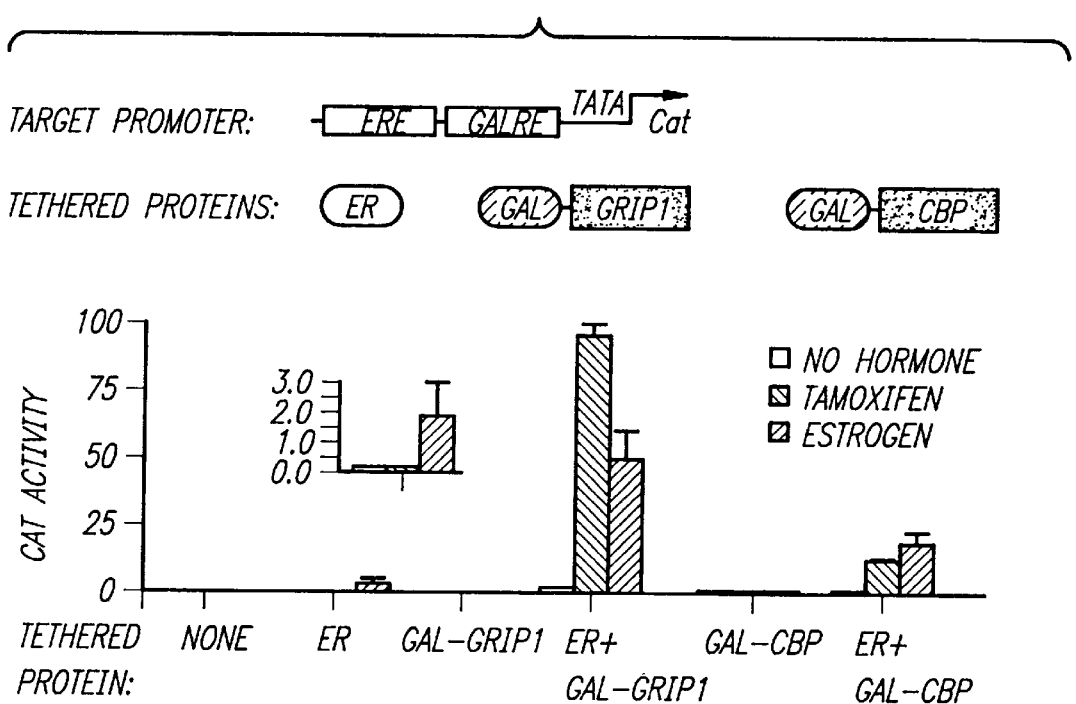
FIG. 9 presents data which demonstrate that tethering a coactivator to the promoter is sufficient to allow the ER AF-1 domain to strongly stimulate transcription. A CAT reporter gene with single adjoining ERE and GALRE sites upstream of a TATA box was transfected into HeLa cells along with expression vectors for ER, ER and GAL-GRIP1, or ER and GAL-CBP in the presence of hormones as indicated.

Another Illustration of the Triggering Concept: Tethering the Transactivator and Coactivators in cis We also asked whether recruiting both a transactivator and coactivator in to the same promoter allowed triggering. We utilized a reporter gene that contained a classical estrogen response element (ERE) and a single GAL-RE in tandem, upstream of the minimal collagenase TATA box. This reporter allows ER and the tethered coactivator to bind simultaneously at the promoter. FIG. 9 shows that with transfected ER, estrogen, but not tamoxifen, elicited a weak response from the reporter gene. This is consistent with previous results which show that isolated AF-1 cannot activate transcription from a simple promoter. Transfected GAL-GRIP1, once again, gave very little activity. In combination, however, ER and GAL-GRIP1 synergised strongly in a manner that was dependent on either estrogen or tamoxifen. Thus, ER and GAL-GRIP1 synergise when placed in combination of the same promoter and this combination is sufficient to change the behavior of tamoxifen from a pure antagonist to a strong agonist.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of identifying test compounds that modulate transcription of a gene of interest by modulating the triggering function of a transcription factor, the method comprising:
   i) contacting a nucleic acid with a tethered coactivator, said nucleic acid comprising a reporter gene operably linked to a response element, and said tethered coactivator comprising:
      a) a polypeptide that comprises an activation function from a transcriptional coactivator; and
      b) a DNA binding moiety that specifically binds to the response element;
   ii) contacting the tethered coactivator with a transcription factor polypeptide that comprises an activation function of a transcription factor that is involved in modulating expression of the gene of interest in its natural milieu, wherein the transcription factor polypeptide is contacted with a test compound prior to contacting the tethered coactivator; and
   iii) detecting expression of the reporter gene wherein an alteration of the expression of the reporter gene as compared to expression of the reporter gene where the transcription factor polypeptide is not contacted with the test compound indicates that said test compound modulates the triggering function of the transcription factor.

2. The method according to claim 1, wherein the method is carried out in a cell.

3. The method according to claim 2, wherein the transcription factor polypeptide is provided by expression of a heterologous gene encoding the transcription factor polypeptide in a cell.

4. The method according to claim 1, wherein said modulating results in activation of said reporter gene.

5. The method according to claim 1, wherein the response element is heterologous to the gene of interest.

6. The method according to claim 1, wherein the transcription factor is a nuclear hormone receptor.

7. The method according to claim 1, wherein the test compound interferes with the ability of the nuclear hormone receptor to become associated with its natural hormone.

8. The method according to claim 1, wherein the test compound acts as a mimetic of a natural hormone in its ability to modulate activity of the nuclear hormone receptor.

9. The method according to claim 6, wherein the transcription factor is an estrogen receptor.

10. A method of identifying test compounds that modulate an indirect estrogen response by modulating the triggering function of an estrogen receptor, the method comprising:
   i) contacting a nucleic acid with a tethered coactivator, said nucleic acid comprising a reporter gene operably linked to an AP-1 site, and said tethered coactivator comprising:
      a) a polypeptide that comprises an activation function from a transcriptional coactivator, and
      b) a DNA binding moiety that specifically binds to the AP-1 site;
   ii) contacting the tethered coactivator with the estrogen receptor, wherein the estrogen receptor is contacted with a test compound prior to contacting the tethered coactivator; and
   iii) detecting expression of the reporter gene wherein an alteration of the expression of the reporter gene as compared to expression of the reporter gene where the estrogen receptor is not contacted with the test compound indicates that said test compound modulates an indirect estrogen response by modulating the triggering function of the estrogen receptor.

11. The method according to claim 10, wherein the estrogen receptor is provided by expression of a heterologous gene encoding said estrogen receptor.

12. The method according to claim 10, wherein said modulating results in activation of said reporter gene.

13. The method according to claim 10, wherein the test compound interferes with the ability of the receptor to become associated with estrogen.

14. The method according to claim 10, wherein the test compound acts as a mimetic of a natural hormone in its ability to modulate activity of the estrogen receptor.

* * * * *